US00PP30765P3

(12) United States Plant Patent
Uchneat

(10) Patent No.: US PP30,765 P3
(45) Date of Patent: Jul. 30, 2019

(54) ***LAGERSTROEMIA* PLANT NAMED 'G2X13377'**

(50) Latin Name: *Lagerstroemia indica*
Varietal Denomination: G2X13377

(71) Applicant: Michael S Uchneat, Bellefonte, PA (US)

(72) Inventor: Michael S Uchneat, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 0 days.

(21) Appl. No.: 15/732,449

(22) Filed: Nov. 15, 2017

(65) Prior Publication Data

US 2019/0150345 P1 May 16, 2019

(51) Int. Cl.
*A01H 5/02* (2018.01)
*A01H 6/00* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./226, 252
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Lagerstroemia* cultivar named 'G2X13377' is disclosed, characterized by white blooms tinged light pink. Plants are low growing, well branched and very floriferous with distinctive light green foliage. The new variety is a *Lagerstroemia*, normally used for outdoor ornamental purposes.

2 Drawing Sheets

Figure 1:
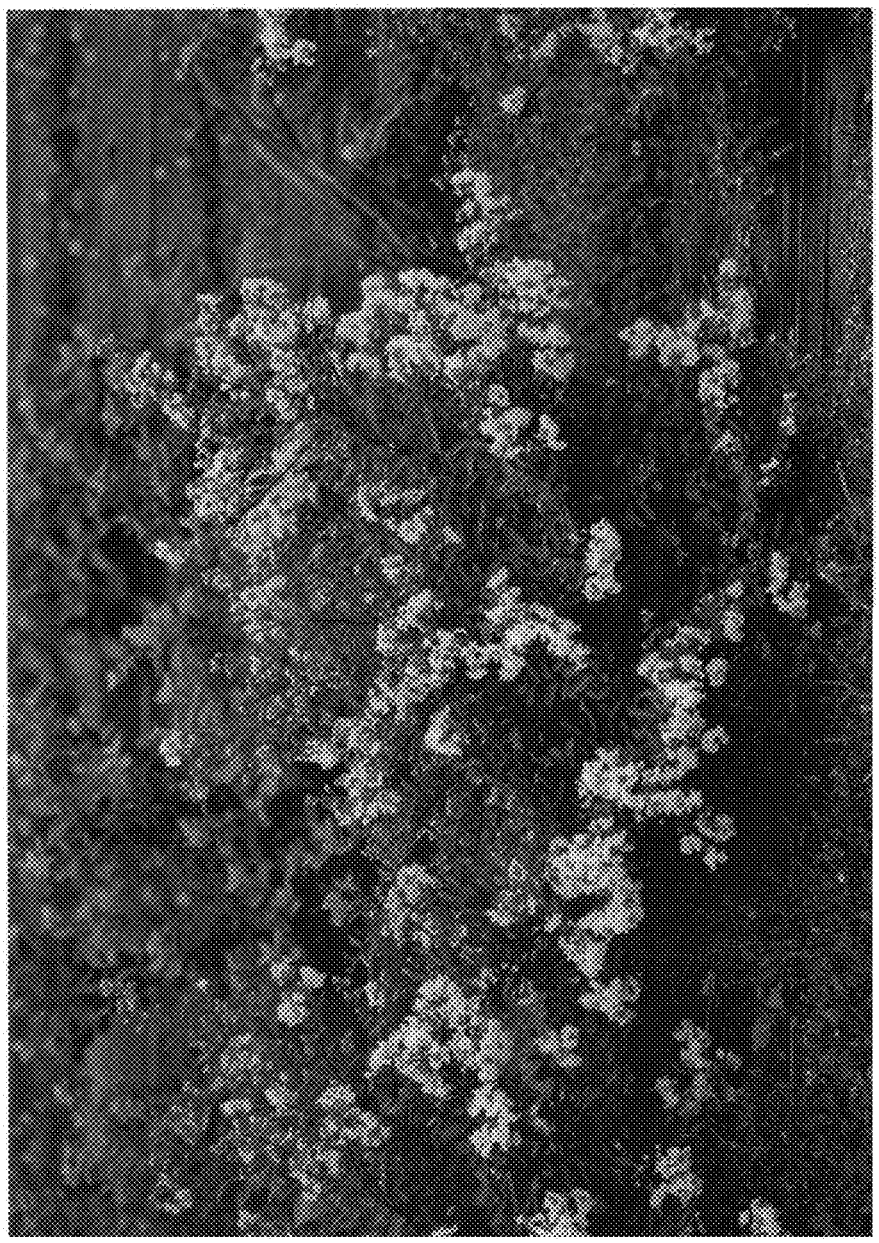

Latin name of the genus and species: *Lagerstroemia indica.*

Variety denomination: 'G2X13377'.

BACKGROUND OF THE INVENTION

The new *Lagerstroemia* cultivar is a product of a planned breeding program conducted by the inventor, Michael Uchneat, in Bellefonte, Pa. The objective of the breeding program was to develop a compact *Lagerstroemia* exhibiting the characteristics of winter hardiness consistently superior to present compact and traditional market genotypes; heat tolerance equal to market genotypes; a fully mounded habit with superior branching and floral coverage; reblooming; multiple colors in a well-matched collection; dark green foliage; powdery mildew resistance; and excellent propagation characteristics from vegetative cutting. The open pollination resulting in this new variety was made during August of 2010.

The seed parent is the unpatented commercial variety referred to as *Lagerstroemia* '13301-1'. The pollen parent is unidentified as more than 15 proprietary pollen parents were used. The new variety was selected September of 2011 by the inventor in a group of seedlings resulting from the 2010 open pollination, in a seedling trial field in Bellefonte, Pa.

Asexual reproduction of the new cultivar was performed by softwood cuttings. This was first performed at Spring Meadow Nursery in Bellefonte, Pa. during February of 2011 and has shown that the unique features of this cultivar are stable and reproduced true to type in multiple successive generations.

SUMMARY OF THE INVENTION

The cultivar 'G2X13377' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G2X13377' These characteristics in combination distinguish 'G2X13377' as a new and distinct *Lagerstroemia* cultivar;

1. Pale pink to white flowers.
2. Light green foliage.
3. Very floriferous.
4. Very well branched, lower growing.

Plants of the new cultivar 'G2X13377' are similar to plants of the seed parent, *Lagerstroemia* '13301-1' in most horticultural characteristics; however, plants of the new cultivar 'G2X13377' differ in the following;

1. The new variety has a white to pink colored flower, the seed parent has a light violet colored flower.
2. The new variety has good basal branching, the seed parent has loose branching.
3. The new variety has good cold tolerance, the seed parent has not as much cold tolerance.

The pollen parent cannot be accurately identified.

COMMERCIAL COMPARISON

Plants of the new cultivar 'G2X13377' are comparable to the commercial variety *Lagerstroemia* 'JD900', U.S. Plant Pat. No. 22,698. The two *Lagerstroemia* varieties are similar in most horticultural characteristics; however, the new variety 'G2X13377' differs in the following;

1. The new variety has light green foliage, comparator's foliage is much darker.
2. New variety's flowers are very pale pink to white, comparator's flowers are white.

3. New variety's new growth wood is grey-brown, comparator's new growth is brown.

BRIEF DESCRIPTION OF THE PHOTOGRAPHS

The accompanying photograph in FIG. 1 illustrates in full color a typical plant of 'G2X13377' grown outdoors in Grand Haven, Mich. in a 3 gallon pot. Age of the plant photographed is approximately 2 to 3 years old from a rooted cutting.

Figure 2:
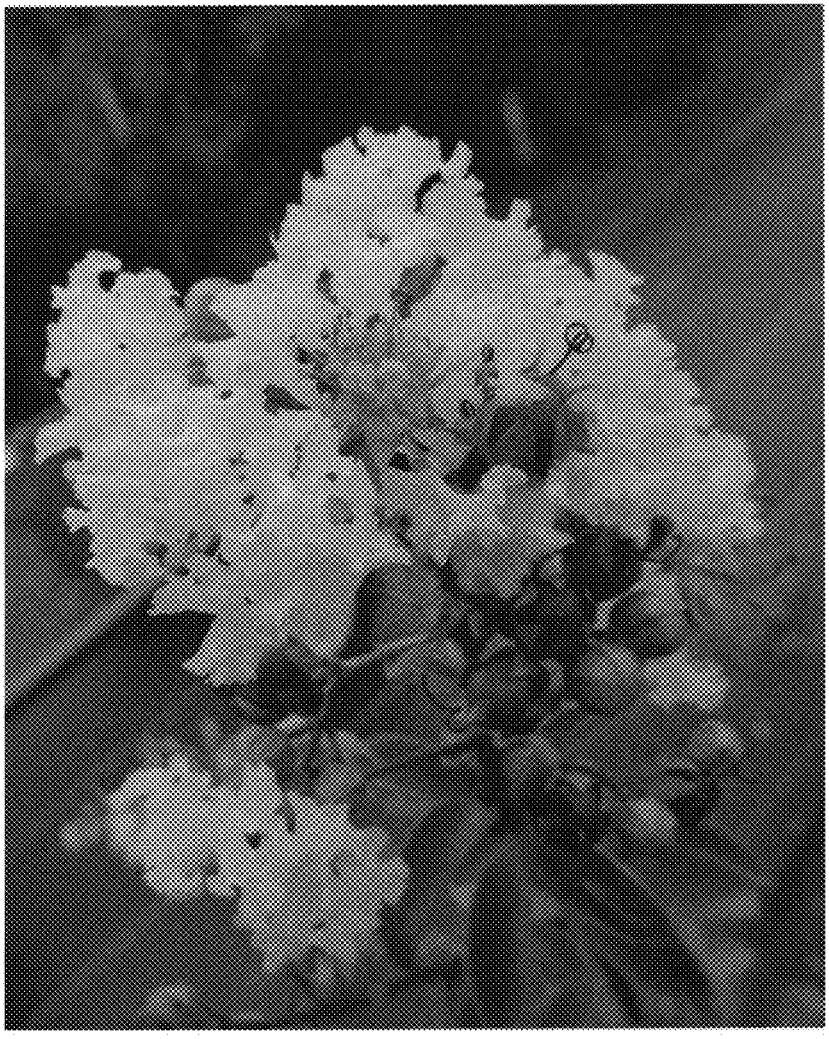

FIG. 2 illustrates a close up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'G2X13377' plants grown in a polyhouse during July of 2017 Grand Haven. Mich. The growing temperature ranged from approximately 18° C. to 27° C. during the day and from approximately 5° C. to 10° C. during the night. General light conditions are normal sunlight and numerical values represent averages of typical plant types.

Botanical classification: *Lagerstroemia indica* 'G2X13377'.

PROPAGATION

Type of propagation typically used: Terminal vegetative cutting.

Time to initiate roots: About 14-21 days at about 24° C.

Time to produce a rooted cutting: About 28-35 days at about 24° C.

Root description: Thin fibrous, not fleshy, freely branching. White in color, not accurately measured with R.H.S. Chart.

PLANT

Age of plant described: 2-3 years old from a rooted cutting.
Container size: 3 gallon container.
Overall plant shape: Upright.
Growth habit: Freely branching.
Plant spread: 108 cm.
Plant height: 90 cm.
Growth rate: Good.
Plant vigor: Good.
Branching habit: Basal, open.
Length of primary lateral branches: 50-70 cm.
Diameter of lateral branches: 5-7 mm.
Quantity of lateral branches: About 20.
Stem:
- *Color*.—Old growth: Green group 135B. Young: Grey brown group 199A.
- *Shape*.—Round.
- *Strength*.—Good.
- *Aspect angle*.—Upright.
- *Texture*.—Pubescent, then woody with age.

Internode length: Average 3.5 cm.

FOLIAGE

Leaf:
- *Arrangement*.—Opposite or sub-opposite.
- *Average length*.—3.5 cm.
- *Average width*.—2 cm.
- *Shape of blade*.—Elliptical.
- *Apex*.—Acute.
- *Base*.—Obtuse.
- *Margin*.—Entire.
- *Texture of top surface*.—Smooth.
- *Texture of bottom surface*.—Smooth.
- *Color*.—Young foliage upper side: Green group 141B. Young foliage under side: Green group 141C. Mature foliage upper side: Green group 141A. Mature foliage under side: Green group 141C.
- *Venation*.—Type: Pinnate. Venation color upper side: Yellow Green 153 A. Venation color under side: Immature-red group 179B. Mature — Greyed-green group 195B.
- *Petiole*.—Length: 1 mm. Diameter: 1 mm. Texture, upper side: Smooth. Texture, under side: Smooth. Color, upper side: Yellow Green 153A. Color, under side: Greyed-green group 195B.

FLOWER

Natural flowering season: June-October.
Inflorescence form: Panicles.
Flowers per inflorescence: About 20 open, about 50 buds.
Inflorescence size:
- *Width*.—17 cm.
- *Height*.—20 cm.

Individual flowers:
- *Type*.—Rotate.
- *Shape*.—Obovate.
- *Habit*.—Whorled outward.
- *Diameter*.—3.5 cm.
- *Length*.—3.5 cm.
- *Depth*.—1.5 cm.
- *Persistence*.—Self-cleaning.
- *Fragrance*.—Floral, very light.

Petals:
- *Arrangement*.—Whorled.
- *Number*.—6.
- *Shape*.—Loosely edged and undulate orbit shape.
- *Margin*.—Loose, undulate.
- *Tip shape*.—Rounded.
- *Base shape*.—Rounded.
- *Length*.—1.5 cm.
- *Width*.—1.25 cm.
- *Texture*.—Upper: Soft, smooth, delicate. Lower: Soft, smooth, delicate.
- *Color*.—When opening: Upper surface: White N155C, very lightly tinged Red 56D. Under surface: White N155C, very lightly tinged Red 56D.. Fully opened: Upper surface: White N155D, occasionally very lightly tinged Red 56D. Under surface: White N155D.

Bud:
- *Shape*.—Sphere.
- *Length*.—7 cm.
- *Diameter*.—8 cm.
- *Color*.—Green group 142C.

Sepals:
*Appearance*.—Smooth, glossy, fused.
*Arrangement*.—Unguiculate.
*Shape*.—Narrowly triangular.
*Tip shape*.—Acute.
*Base shape*.—Obtuse.
*Margin*.—Entire.
*Quantity per flower*.—6.
*Length*.—9 mm.
*Width*.—3.2 mm.
*Margin*.—Entire.
*Texture*.—Upper: Smooth, coriaceous, rugose. Lower: Smooth.
*Color*.—Upper: Green 142C. Lower: Greyed-Green 192A.

Calyx:
*Shape*.—Unguiculate.
*Length*.—1.1 mm.
*Diameter*.—9 mm.

Peduncle:
*Length*.—1 cm.
*Diameter*.—0.5-1 mm.
*Texture*.—Smooth.
*Color*.—Yellow-Green 145B blended with Red-Purple 60A.
*Orientation*.—Upright and outward.
*Strength*.—Good.

Pedicel:
*Length*.—1.3 cm.
*Diameter*.—8 mm.
*Angle*.—<45 degrees.
*Strength*.—Good.
*Texture*.—Smooth, slightly pubescent.
*Color*.—Greyed-red 182A.

REPRODUCTIVE ORGANS

Stamens:
*Number*.—About 30.
*Filament length*.—1 cm.
*Filament color*.—White 155D.

Anthers:
*Shape*.—Linear.
*Length*.—1 mm.
*Color*.—Yellow group 13A.
*Pollen*.—Amount: Moderate. Color: Yellow 13A.

Pistil:
*Number*.—1.
*Length*.—1.5 cm.

Stigma:
*Shape*.—Globe.
*Color*.—Orange-red N34A.
*Ovary color*.—Green-yellow 1D.

OTHER CHARACTERISTICS

Fruits and seeds: Not observed to date.

Disease/pest resistance: Neither resistance nor susceptibility to normal diseases and pests of *Lagerstroemia* observed.

Temperature range: Observed to tolerate a temperature range from −28° C. to 35° C. Root hardy to −28C, top of the plant does die back to the ground.

What is claimed is:

1. A new and distinct cultivar of *Lagerstroemia* plant named 'G2X13377' as herein illustrated and described.

* * * * *